(12) United States Patent
Devisetty et al.

(10) Patent No.: US 9,161,535 B2
(45) Date of Patent: Oct. 20, 2015

(54) COLOR STABLE AQUEOUS FORMULATIONS CONTAINING THE POTASSIUM SALT OF (S)-(+)-ABSCISIC ACID AND METHODS OF THEIR USE

(71) Applicant: Valent BioSciences Corporation, Libertyville, IL (US)

(72) Inventors: Bala N. Devisetty, Buffalo Grove, IL (US); John Lopez, Gurnee, IL (US); Daniel F. Heiman, Libertyville, IL (US); Peter D. Petracek, Grayslake, IL (US); Xiaozhong Liu, Vernon Hills, IL (US); Derek D. Woolard, Zion, IL (US); Gregory D. Venburg, Deerfield, IL (US); Yueh Wang, Arlington Heights, IL (US); Prem Warrior, Chicago, IL (US)

(73) Assignee: Valent BioSciences Corporation, Libertyville, IL (US)

( * ) Notice: Subject to any disclaimer, the term of this patent is extended or adjusted under 35 U.S.C. 154(b) by 0 days.

(21) Appl. No.: 14/336,436

(22) Filed: Jul. 21, 2014

(65) Prior Publication Data
US 2014/0329685 A1    Nov. 6, 2014

Related U.S. Application Data

(63) Continuation-in-part of application No. 14/275,056, filed on May 12, 2014, which is a continuation of application No. 13/447,715, filed on Apr. 16, 2012, now Pat. No. 8,722,928, which is a continuation-in-part of application No. 12/011,846, filed on Jan. 30, 2008, now Pat. No. 8,318,976.

(60) Provisional application No. 60/898,550, filed on Jan. 31, 2007.

(51) Int. Cl.
| | | |
|---|---|---|
| C07C 63/06 | (2006.01) | |
| A01N 31/08 | (2006.01) | |
| A01N 37/42 | (2006.01) | |

(52) U.S. Cl.
CPC ............... *A01N 37/42* (2013.01); *A01N 31/08* (2013.01); *C07C 63/06* (2013.01)

(58) Field of Classification Search
USPC ................................................. 562/508, 509
See application file for complete search history.

(56) References Cited

U.S. PATENT DOCUMENTS

| | | | |
|---|---|---|---|
| 4,209,530 A | 6/1980 | Visscher | |
| 4,434,180 A | 2/1984 | Visscher | |
| 5,201,931 A | 4/1993 | Abrams et al. | |
| 5,518,995 A | 5/1996 | Abrams et al. | |
| 6,004,905 A | 12/1999 | Abrams et al. | |
| 6,074,986 A | 6/2000 | Mulqueen et al. | |
| 6,455,471 B1 | 9/2002 | Gubelmann-Bonneau et al. | |
| 6,586,617 B1 * | 7/2003 | Tabuchi et al. | ................ 558/394 |
| 2008/0207454 A1 | 8/2008 | Heiman et al. | |

FOREIGN PATENT DOCUMENTS

GB    1251867    11/1971

OTHER PUBLICATIONS

International Search Report and Written Opinion issued Aug. 30, 2013.
Mauseth, "Botany an introduction to plant biology", 1991 Philadelphia Saundera pp. 348-415.
Raven et al., Biology of plants fifth edition, 1992 New York Worth. pp. 545-572.
Milborrow, "The chemistry and physiology of abscisic acid", Am. Rev. Plant Physiol, 1974, 25 pp. 259-307.
Zhang et al., "Purification and identification of a 42-kilodalton abscisic acid-specific-binding protein from epidermis of broad bean leaves", Feb. 2002, Plant Physiology, vol. 128, pp. 714-725.
Finkelstein et al., "Abscisic Acid Biosynthesis and Response", 2002 The *Arabidopsis* Book, American Society of Plant Biologists, pp. 1-52.
Railton et al., "Effects of Abscisic Aid on the Levels of Endogenous Gibberellin-like Substances in *Solanum Andigena*", Plants (berl.) 112, 1973, pp. 65-69.
Blumenfeld et al., "Cuticular Penetration of Abscisic Acid", Planta (Berl.) 107, 1972, pp. 261-268.
Bonnafous et al., "Mouvelle Methode Dc Resolution Optique de L'Acide Abscisique", Tetrahedron Letters No. 13, 1973, pp. 1119-1122.
Yu et al., "Abscisic Acid Stimulates a Calcium-Dependent Protein Kinnse in Grape Berry", Plant Physiology, vol. 140, Feb. 2006, pp. 558-579.
Kriedemann et al., "Abscisic Acid and Stomatal Regulation", Plant Physiology, 49, 1972, pp. 842-847.
Zeevart et al., "Metabolism and Physiology of Abscisic Acid", Ann. Rev. Plant Physiol Plant Mol. Biol., 39 1988, pp. 439-473.

* cited by examiner

*Primary Examiner* — Kamal Saeed
*Assistant Examiner* — Janet L Coppins
(74) *Attorney, Agent, or Firm* — Wood, Phillips, Katz, Clark & Mortimer

(57) ABSTRACT

The present invention generally relates to color stable formulations containing the potassium salt of (S)-(+)-abscisic acid, the color stabilizers sodium citrate and sodium acetate, the antimicrobial agent potassium sorbate, and do not contain an acrylic copolymer surfactant. The present invention is also directed to methods for using the present formulations in organic farming.

20 Claims, No Drawings

COLOR STABLE AQUEOUS FORMULATIONS CONTAINING THE POTASSIUM SALT OF (S)-(+)-ABSCISIC ACID AND METHODS OF THEIR USE

RELATED APPLICATIONS

This application is a continuation-in-part of U.S. application Ser. No. 14/275,056 filed May 12, 2014, which is a continuation of U.S. application Ser. No. 13/447,715, filed Apr. 16, 2012, which issued on May 13, 2014 as U.S. Pat. No. 8,722,928, which is a continuation-in-part of U.S. application Ser. No. 12/011,846, filed Jan. 30, 2008, which issued on Nov. 27, 2012 as U.S. Pat. No. 8,318,976, which claims the benefit of U.S. Provisional Application Ser. No. 60/898,550 filed Jan. 31, 2007. The entire teachings of the above-referenced applications are incorporated herein by reference.

FIELD OF THE INVENTION

The present invention generally relates to color stable formulations containing the potassium salt of (S)-(+)-abscisic acid and methods of their use in organic farming.

BACKGROUND

Abscisic acid ("(S)-(+)-abscisic acid" or "S-ABA") is a naturally occurring plant hormone which is found in all higher plants. (S)-(+)-abscisic acid is involved in many major processes during plant growth and development including dormancy, germination, bud break, flowering, fruit set, general growth and development, stress tolerance, ripening, maturation, organ abscission, and senescence. (S)-(+)-abscisic acid also plays an important role in plant tolerance to environmental stresses, such as drought, cold, and excessive salinity.

The naturally occurring enantiomeric form of abscisic acid is (S)-(+)-abscisic acid. In some literature reports the other enantiomer, (R)-(−)-abscisic acid is seen to be biologically inactive. In other research, it has been reported that (R)-(−)-abscisic acid also has some biological activities, however, they are often different from those of the (S)-(+)-enantiomer. See, Zeevart, J. A. D. and Creelman, R. A. (1988) *Metabolism and Physiology of Abscisic Acid*, Annu. Rev. Plant Physiol. Plant Mol. Biol. 39, 439-473. Thus, for use in a commercial agricultural product, the formulations of the present invention comprising (S)-(+)-abscisic acid as the active ingredient are preferable to the prior art formulations comprising racemic (R,S)-(±)-abscisic acid, because, in the best case for these prior art formulations, half of the racemic (R,S)-(±)-abscisic acid is inert, resulting in the need to purchase, formulate, package, ship, and apply twice as much material. In the worst case, the (R)-(−)-enantiomer in racemic (R,S)-(±)-abscisic acid can add undesirable side effects to the desired result given by the applied (S)-(+)-abscisic acid and potentially result in undesirable residue in food crops and in the environment.

The stereochemistry of the side chain of naturally occurring abscisic acid produced biosynthetically by all green plants and some microorganisms is 2-cis-,4-trans. The (S)-(+)-2-trans-,4-trans-isomer of abscisic acid also occurs naturally, being produced photolytically by the action of sunlight on the (S)-(+)-2-cis-,4-trans-isomer. The (S)-(+)-2-trans-,4-trans-isomer is reported to be biologically inactive. See, P. E. Kreidelmann, et al., Plant Physiol. 49, 842-847 (1972), D. P. Zhang, et al., Plant Physiol. 128, 714-725, (2002) or X. C. Yu, et al., Plant Physiol. 140, 558-579 (2006).

A challenge with agricultural formulations of (S)-(+)-abscisic acid salts is the inability to maintain color stability. Previously, the color of aqueous formulations of (S)-(+)-abscisic acid changed during storage from a near colorless solution to a dark yellow or brown solution. Such a result is undesirable because the formulation can have an inconsistent cosmetic appearance which raises questions regarding formulation quality and efficacy and can lower the product's commercial appeal. Therefore, there is an unmet need in the art for (S)-(+)-abscisic acid salt formulations with color stability.

Sodium citrate and sodium acetate are both listed in the Food and Drug Administration's ("FDA") Select Committee on Generally Regarded as Safe Substances ("SCOGS") Database, and therefore, are desirable alternatives to color stabilizers utilized by the prior art that are undesirable or prohibited in pesticide formulations used on food crops in the United States.

U.S. Pat. No. 8,722,928 is directed to aqueous formulations containing salts of (S)-(+)-abscisic acid, the acrylic copolymer surfactant Atlox™ 4913, and the color stabilizers sodium citrate and sodium acetate. The formulations of U.S. Pat. No. 8,722,928 have impressive color stability and are non-precipitating. While the formulations of U.S. Pat. No. 8,722,928 have desirable and commercially important qualities, they are not suitable for organic farming.

The Organic Materials Review Institute ("OMRI") reviews agricultural products against organic standards to certify that products are appropriate for use in organic farming. Some of the organic standards include that the ingredients of the products are not obtained from genetically modified organisms, that all of the inert ingredients are included in the EPA List 4 §205.601(m), and that the natural products are extracted by methods that meet the 7 C.F.R. §205 criteria.

One of the advantages of the formulations of U.S. Pat. No. 8,722,928 is that they can be tank-mixed with the plant growth regulator ethephon without the formation of precipitates. This attribute, however, is not important to organic farmers because ethephon cannot be used in organic farming.

Therefore, there is a need for environmentally safe, non-phytotoxic, efficacious, ABA solution formulations for use in organic farming. The improved formulations should overcome the color stability, handling, storage, transportation, and solubility issues encountered by prior art formulations. The formulations should also be certified by OMRI to be safe for organic farming and be safe for end users.

SUMMARY OF THE INVENTION

Applicants were unexpectedly able to develop a formulation that meets OMRI standards while maintaining satisfactory color stability.

The present invention is generally directed to color stable formulations that contain the potassium salt of (S)-(+)-abscisic acid but do not contain an acrylic copolymer surfactant. The present invention is also directed to methods for using the organic formulations in organic farming.

The present invention allows for improved concentrated formulations of (S)-(+)-abscisic acid that are more convenient to package, store, transport, handle, and apply to plants. These improved concentrated formulations are highly resistant to discoloration even under prolonged harsh environmental storage conditions. Further, these improved concentrated formulations can be easily mixed with water and some additional plant growth regulators without the formation of precipitates. Importantly, the formulations of the present invention can be used in organic farming.

Formulations of the present invention generally comprise from about 0.25 to about 45 weight % of the formulation of (S)-(+)-abscisic acid as a potassium salt, from about 0.1 to about 1.0 weight % of sodium citrate, from about 0.1 to about 1.0 weight % of sodium acetate, from about 0.01 to about 1.0 weight % of potassium sorbate, and do not contain an acrylic copolymer surfactant, such as Atlox™ 4913. Other components which enhance the long-term storage stability or the biological activity of the (S)-(+)-abscisic acid may optionally be included.

DETAILED DESCRIPTION OF THE INVENTION

The present invention relates to aqueous formulations of the potassium salt of (S)-(+)-abscisic acid. Abscisic acid is an optically active 15-carbon carboxylic acid. The structural formula of 2-cis-,4-trans-(S)-(+)-abscisic acid is set forth below:

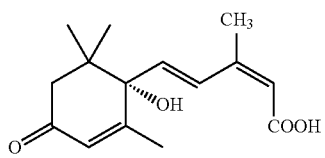 [SMILES: CC1=CC(=O)CC(C)(C)[C@@]1(O)/C=C/C(C)=C\C(=O)O]

The aqueous formulations of the present invention utilize the (S)-(+)-enantiomer and the 2-cis-,4-trans-stereochemistry of the carbon chain rather than a racemic mixture of enantiomers and any of the other possible combinations of stereochemistry of the molecule. Unless expressly stated otherwise, in all instances when the Application refers to abscisic acid, S-ABA, or (S)-(+)-abscisic acid, it refers specifically to 2-cis-,4-trans-(S)-(+)-abscisic acid.

Liquid formulations of the present invention can be prepared as either ready-to-use dilutions or dilutable concentrates. According to the present invention, a formulation containing from 0.25% to as much as 45% by weight of (S)-(+)-abscisic acid can be obtained at a pH of about 6.0 to about 7.0. The dilutable concentrates can be diluted into water directly to a final application concentration or to any intermediate concentration, without risk of precipitation of the active ingredient as long as the buffering capacity of the formulation is not exceeded. The liquid formulations of the present invention are safe to handle and use and the (S)-(+)-abscisic acid active ingredient is color stable and does not precipitate under various expected storage, shipping, and use conditions. Applicants' formulations are a significant improvement over formulations of the prior art for treating plants. A person having ordinary skill in the art would be able to determine how to prepare the final aqueous solution concentration for direct application to plants, or how to prepare any intermediate dilutions for use in chemigation equipment or injection diluters or similar equipment, without undue experimentation and without causing precipitation of the active ingredient or other formulation components.

The end user can apply formulations of the present invention to plants for various purposes, including but not limited to improving stress tolerance, improving water use efficiency, slowing the rate of water transpiration, temporarily reducing the growth rate, manipulating the flowering process, and improving the quality and color of fruits. The possible uses may also include, for example, distribution and sale of various concentrated solutions of (S)-(+)-abscisic acid. Utilizing such high concentrations for shipping and handling allows the use of smaller volumes of water, thus simplifying shipping and handling procedures and decreasing costs. The end user could then dilute the product to a 1% concentration (or other percentage depending on the end user's needs) and fill the supply reservoir of mixing equipment for spray or drench application to greenhouse plants. Alternatively, another end user could prepare a diluted solution for injection into a drip irrigation system for a vineyard at the appropriate time to enhance the color of a wine or table grape crop.

Applicants have found that the formulations containing (S)-(+)-abscisic acid as the potassium salt show significant improvement over formulations in the prior art for treating plants. Specifically, Applicants' have found that the formulations of this invention containing (S)-(+)-abscisic acid as the potassium salt can be used in a wide range of concentrations and on a wide range of crops. For example, the formulations of the present invention can be used to accelerate and enhance the development of red coloration in red grape berries, allowing harvesting to begin earlier than would otherwise be possible, and allowing for higher vineyard yields because fewer bunches remain unharvested due to poor coloration. The harvest quality parameters and the storage characteristics of the grapes treated before harvest with the formulations of the present invention alone are superior to those of grapes treated with ethephon alone, which has been the accepted practice in the prior art. The formulations of the present invention can be applied to vegetable seedling transplants before and/or after transplanting to temporarily slow their growth, reduce transplant shock, enhance crop establishment after transplant, and increase the plant's resistance to stress events. Formulations of the present invention can be applied to leafy vegetables and herbs to slow their growth and manage the timing of harvest. Ornamental plants can be treated with the formulations of the present invention, significantly reducing transpiration and delaying wilting caused by environmental stress thereby resulting in more desirable plants compared to untreated plants.

Formulations of the present invention may be used to treat vegetable crops in one or more applications to vegetable seedlings or older plants to reduce plant growth, reduce crop stress, and enhance post-harvest crop quality. Vegetable crops include, but are not limited to: fruiting vegetables such as tomato and pepper; cucurbits such as cucumbers and melons; *brassica* vegetables such as broccoli and cabbage; leafy vegetables and herbs such as celery, spinach, lettuce, beet greens, arugula and other leafy greens, fennel, basil and other herbs.

Formulations of the present invention may be used to treat ornamental crops such as potted flowering plants, bedding plants, perennial, nursery, and foliage plants in one or more applications by drench, sprench, spray, flood, or chemigation to reduce water use, conserve water, withstand environmental stress and control growth. An effective amount of (S)-(+)-abscisic acid as the potassium salt in an application solution for ornamental plants is from about 25 to about 2,000 ppm and the effective amount of (S)-(+)-abscisic acid as the potassium salt applied per application is from about 0.047 to about 5.678 g per 100 sq ft. More preferably, an effective amount of (S)-(+)-abscisic acid as the potassium salt in an application solution for ornamental plants is from about 125 to about 500 ppm and the effective amount of (S)-(+)-abscisic acid as the potassium salt applied per application is from about 0.237 to about 1.42 g per 100 sq ft.

Presently, the most preferred antimicrobial agent is potassium sorbate, however, suitable alternatives known by those skilled in the art may be used. When formulations of the present invention are intended for long term storage or for distribution and commercial sale to the user, it is advantageous to incorporate the antimicrobial agent at a concentration of from about 0.01% to about 1.0% by weight, more preferably from about 0.1 to about 0.75%, and most preferably at about 0.25%.

The concentration of the color stabilizers, sodium citrate and sodium acetate, in formulations of the present invention can be from about 0.1% to about 1.0%, and more preferably from about from about 0.2% to about 1.0% or from about 0.25 to about 0.75%, with the most preferred amount being about 0.5% for each color stabilizer.

In one embodiment, the present invention is directed to an aqueous formulation for the treatment of organically grown plants comprising from about 0.25 to about 45 weight % of the formulation of (S)-(+)-abscisic acid as the potassium salt, from about 0.1 to about 1.0 weight % of sodium citrate, from about 0.1 to about 1.0 weight % of sodium acetate, from about 0.01 to about 1.0 weight % potassium sorbate, optionally one or more performance enhancing additives, and the formulations do not contain an acrylic copolymer surfactant.

In a preferred embodiment, the formulations contain from about 5 to about 20 weight % of (S)-(+)-abscisic acid as the potassium salt. In a more preferred embodiment, the formulations contain from about 7 to about 15 weight % of (S)-(+)-abscisic acid as the potassium salt. In a most preferred embodiment, the formulations contain about 10.0 weight % of (S)-(+)-abscisic acid as the potassium.

In another preferred embodiment, the formulations contain from about 0.2 to about 1.0 weight % of sodium citrate and from about 0.2 to about 1.0 weight % of sodium acetate.

In another embodiment, the formulations of the present invention contain from about 5 to about 20 weight % of (S)-(+)-abscisic acid as the potassium salt, from about 0.25 to about 0.75 weight % of sodium citrate, from about 0.25 to about 0.75 weight % of sodium acetate, from about 0.1 to about 0.75 weight % of potassium sorbate, and the formulations do not contain an acrylic copolymer surfactant.

In a preferred embodiment, the formulations of the present invention contain about 10.0 weight % of (S)-(+)-abscisic acid as the potassium salt, about 0.5 weight % of sodium citrate, about 0.5 weight % of sodium acetate, about 0.25 weight % of potassium sorbate, and the formulations do not contain an acrylic copolymer surfactant.

In another embodiment, the formulations of the present invention consist of from about 0.25 to about 45 weight % of (S)-(+)-abscisic acid as the potassium salt, from about 0.1 to about 1.0 weight % of sodium citrate, from about 0.1 to about 1.0 weight % of sodium acetate, from about 0.01 to about 1.0 weight % of potassium sorbate, and optionally one or more performance enhancing additives.

The formulations of the present invention also include a sufficient quantity of an agriculturally acceptable and OMRI approved solvent. One preferred solvent is water.

Other embodiments of the present invention include methods of applying the formulations of the present invention to an organically grown crop. In a preferred embodiment, the formulations of the present invention are applied to grapes, vegetables or row crops.

When the formulations of the present invention are applied to grapes, they are preferably applied at a rate of from about 25 to about 1,000 grams per hectare (g/Ha) of (S)-(+)-abscisic acid as the potassium salt. More preferably, they are applied at a rate of from about 183 to about 370 g/Ha of (S)-(+)-abscisic acid as the potassium salt.

When the formulations of the present invention are applied to grapes, they are preferably applied at concentration of from about 10 to about 10,000 parts per million (ppm) of (S)-(+)-abscisic acid as the potassium salt. More preferably, they are applied at a rate of from about 100 to about 500 ppm of (S)-(+)-abscisic acid as the potassium salt.

When the formulations of the present invention are applied to vegetables, they are preferably applied to fruiting vegetables, cucurbits, *brassica* vegetables, leafy vegetables or herbs.

When the formulations of the present invention are applied to vegetables in a greenhouse, they are preferably applied at a rate of from about 0.047 to about 18.93 grams per 100 square feet (g/100 ft$^2$) of (S)-(+)-abscisic acid as the potassium salt.

When the formulations of the present invention are applied to vegetables in a field, they are preferably applied at a rate of from about 11.7 to about 1,871 grams per hectare (g/Ha) of (S)-(+)-abscisic acid as the potassium salt.

When the formulations of the present invention are applied to row crops, they are preferably applied to corn, wheat, soybeans, rice, sugar beets, or cotton.

As used herein, a "row crop" refers to a crop that can be planted in rows wide enough so that it can cultivated by agricultural machinery.

When the formulations of the present invention are applied to row crops in a field, they are preferably applied at a rate of from about 1 to about 1,000 grams per hectare (g/Ha) of (S)-(+)-abscisic acid as the potassium salt. More preferably from about 10 to about 100 grams per hectare (g/Ha) of (S)-(+)-abscisic acid as the potassium salt.

As used herein, "organically grown" refers to the practice of growing plants without the use of genetically modified organisms or products not approved by OMRI.

As used herein, all numerical values relating to amounts, weight percentages and the like, are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The phrase "effective amount" of a component means a sufficient amount of the component to provide the desired biological or chemical effect without at the same time causing additional negative effects. The amount of (S)-(+)-abscisic acid or of another formulation component that is "effective" will vary from formulation to formulation, depending on the particular agricultural use, the particular salt or salts, and the like. Thus, it is not always possible to specify an exact "effective amount." However, an appropriate "effective amount" in any individual case may be determined by one of ordinary skill in the art using routine experimentation.

The disclosed embodiments are simply exemplary embodiments of the inventive concepts disclosed herein and should not be considered as limiting, unless the claims expressly state otherwise.

The following examples are intended to illustrate the present invention and to teach one of ordinary skill in the art how to make and use the invention. They are not intended to limit the invention or its protection in any way.

EXAMPLES

Example 1

Preparation of an Aqueous Formulation Comprising the Potassium Salt of (S)-(+)-Abscisic Acid An aqueous formulation was prepared comprising (S)-(+)-abscisic acid (97.7%) at a concentration of about 10.2% (10%) by weight of the total volume. The solution also contained 0.25% by weight of potassium sorbate, 0.50% by weight of sodium citrate, 0.50% by weight of sodium acetate, 4.50% by weight of potassium hydroxide, and 83.8% by weight of water. The solution had a final pH between 6.2 and 6.6.

Example 2

Freeze and Thaw Stability Study

The formulation of Example 1 was subjected to a study involving seven cycles of freezing and subsequent thawing per industry testing standards. At the end of the seventh cycle, a visual analysis was performed and it was determined that the formulation was stable.

Example 3

Accelerated Two-Week Stability Study

The formulation of Example 1 was subjected to a study involving keeping the formulation in PET bottles for 2 weeks at temperature of 54° C. per industry testing standards. At the conclusion of the study it was determined that the formulation remained stable.

Example 4

Dilution Stability Studies

The formulation of Example 1 was subjected to a study involving diluting the formulation with water. The formulation was diluted with WHO water to a concentration of 5000 ppm of ABA. The dilution remained stable. Similarly, the formulation was diluted with hard water to a concentration of 5000 ppm and the dilution remained stable.

Example 5

Color Stability Study

The formulation of Example 1 was subjected to high temperature conditions (54° C.) to accelerate the development of discoloration per industry testing standards. The color of the formulation was then visually rated using the Gardner color scale, in which the numeric values range from 1 (near colorless) to 18 (deeply colored). At the conclusion of the study it was determined that the formulation of Example 1 had an excellent color rating of only 3.5.

The invention claimed is:

1. An aqueous color stable formulation for the treatment of organically grown plants comprising from about 0.25 to about 45 weight % of (S)-(+)-abscisic acid as the potassium salt, from about 0.1 to about 1.0 weight % of sodium citrate, from about 0.1 to about 1.0 weight % of sodium acetate, from about 0.01 to about 1.0 weight % of potassium sorbate, and optionally one or more performance enhancing additives, wherein the formulation does not contain an acrylic copolymer surfactant.

2. The formulation of claim 1 wherein the formulation comprises about 10.0 weight % of (S)-(+)-abscisic acid as the potassium salt.

3. The formulation of claim 1 wherein the formulation comprises from about 0.2 to about 1.0 weight % of sodium citrate and from about 0.2 to about 1.0 weight % of sodium acetate.

4. The formulation of claim 1, wherein the formulation comprises from about 5 to about 20 weight % of (S)-(+)-abscisic acid as the potassium salt, from about 0.25 to about 0.75 weight % of sodium citrate, from about 0.25 to about 0.75 weight % of sodium acetate, and from about 0.1 to about 0.75 weight % of potassium sorbate.

5. The formulation of claim 1, wherein the formulation comprises about 10.0 weight % of (S)-(+)-abscisic acid as the potassium salt, about 0.5 weight % of sodium citrate, about 0.5 weight % of sodium acetate, and about 0.25 weight % of potassium sorbate.

6. A method of treating an organically grown plant comprising applying to the plant an effective amount of the formulation of claim 1.

7. The method of claim 6 wherein the plant is selected from the group consisting of grapes, vegetables and row crops.

8. The method of claim 7 wherein the plant is grapes.

9. The method of claim 8 wherein the (S)-(+)-abscisic acid as the potassium salt is applied at a rate of from about 25 to about 1,000 grams per hectare (g/Ha).

10. The method of claim 8 wherein the (S)-(+)-abscisic acid as the potassium salt is applied at a rate of from about 183 to about 370 g/Ha.

11. The method of claim 8 wherein the (S)-(+)-abscisic acid as the potassium salt is applied at a concentration of from about 10 to about 10,000 parts per million (ppm).

12. The method of claim 8 wherein the (S)-(+)-abscisic acid as the potassium salt is applied at a concentration of from about 100 to about 500 parts per million (ppm).

13. The method of claim 7 wherein the plant is a vegetable.

14. The method of claim 13 wherein the vegetable is selected from the group consisting of fruiting vegetables, cucurbits, brassica vegetables, leafy vegetables and herbs.

15. The method of claim 13 wherein the (S)-(+)-abscisic acid as the potassium salt is applied to the vegetables in a greenhouse at a rate of from about 0.047 to about 18.93 grams per 100 square feet (g/100 ft$^2$).

16. The method of claim 13 wherein the (S)-(+)-abscisic acid as the potassium salt is applied to the vegetables in a field at a rate of from about 11.7 to about 1,871 grams per hectare (g/Ha).

17. The method of claim 7 wherein the plant is a row crop.

18. The method of claim 17 wherein the row crop is selected from the group consisting of corn, wheat, soybeans, rice, sugar beets, and cotton.

19. The method of claim 17 wherein the (S)-(+)-abscisic acid as the potassium salt is applied at a rate of from about 0.047 to about 5.678 grams per 100 square feet (g/100 ft$^2$).

20. An aqueous color stable formulation for the treatment of organically grown plants consisting of from about 0.25 to about 45 weight % of (S)-(+)-abscisic acid as the potassium salt, from about 0.1 to about 1.0 weight % of sodium citrate, from about 0.1 to about 1.0 weight % of sodium acetate, from about 0.01 to about 1.0 weight % of potassium sorbate, and optionally one or more performance enhancing additives.

* * * * *